United States Patent [19]

Faggian et al.

[11] Patent Number: 4,843,184

[45] Date of Patent: * Jun. 27, 1989

[54] PROCESS FOR EXTRACTING PARAFFINS FROM THEIR MIXTURES WITH PARAFFINSULFONIC ACIDS

[75] Inventors: Lucio Faggian, San Donato Milanese; Maurizio Castellano, Turin; Edoardo Platone, San Donato Milanese; Cosimo Franco, Locri, all of Italy

[73] Assignees: Eniricerche S.p.A., Milan; Enichem Augusta S.p.A., Palermo, both of Italy

[ * ] Notice: The portion of the term of this patent subsequent to Jan. 17, 2006 has been disclaimed.

[21] Appl. No.: 71,872

[22] Filed: Jul. 10, 1987

[30] Foreign Application Priority Data

Jul. 23, 1986 [IT] Italy ................................ 21224 A/86

[51] Int. Cl.$^4$ ............................................ C07C 143/24
[52] U.S. Cl. .................................... 585/864; 585/833; 208/24; 260/505 P
[58] Field of Search .................. 585/833, 864; 208/24, 208/27; 260/505 P, 505 S, 505 A

[56] References Cited

U.S. PATENT DOCUMENTS

| | | | |
|---|---|---|---|
| 2,875,257 | 2/1959 | Thompson | 260/505 P |
| 3,033,898 | 5/1962 | Bray | 260/505 P |
| 3,861,442 | 8/1972 | Bloch et al. | 585/864 |
| 4,269,789 | 5/1981 | Zornes | 260/505 P |
| 4,361,520 | 11/1982 | Luetzelschwab | 260/505 P |

OTHER PUBLICATIONS

Patrick et al., "Supercritical Extraction (SCE) of Dixylenol Sulfone (DXS)", Process Technology Processing, 1985, vol. 3, pp. 379–384.

*Primary Examiner*—Glenn Caldarola
*Attorney, Agent, or Firm*—Morgan & Finnegan

[57] ABSTRACT

Mixtures of $C_{12}$–$C_{18}$ n-paraffins with paraffinsulfonic acids having the same number of carbon atoms, water and sulfuric acid, and obtained by sulfoxidation of said paraffins with sulfur dioxide and oxygen in the presence of water and ultraviolet radiation are stripped of their excess sulfur dioxide and decanted to separate most of the paraffins, and obtain a residual mixture.

The residual mixture is fed with sulfuric acid until a two-phase system forms or at least until the mixture becomes turbid, and the turbid mixture or that floating on the heavy water-sulfuric acid phase is extracted with supercritical carbon dioxide, which removes with it the paraffins, which can be reused in the sulfoxidation process.

11 Claims, No Drawings

PROCESS FOR EXTRACTING PARAFFINS FROM THEIR MIXTURES WITH PARAFFINSULFONIC ACIDS

This invention relates to a process for extracting n-paraffins from their mixtures with paraffinsulfonic acids.

Paraffinsulfonic acids containing between 12 and 18 carbon atoms are generally prepared by sulfoxidation of $C_{12}$–$C_{18}$ paraffins with sulfur dioxide ($SO_2$) and oxygen ($O_2$) in the presence of water ($H_2O$), using ultraviolet (UV) radiation for reaction initiation.

The reaction product obtained from the sulfoxidation reaction consists of a mixture containing small percentages of paraffinsulfonic acids, $H_2O$ and sulfuric acid ($H_2SO_4$), but mostly unreacted n-paraffins.

Most of the n-paraffins can be easily separated from said mixture, but a substantial fraction of them will remain together with the $H_2SO_4$, the $H_2O$ and the paraffinsulfonic acids. It is important to note that the n-paraffins must be separated to the maximum possible extent not only for obvious economic reasons, but also because their presence in paraffinsulfonic acids is undesirable.

The known art gives suggestions for separating n-paraffins from the rest of the $H_2SO_4$, paraffinsulfonic acid and $H_2O$ mixture. One of these suggestions is contained in European patent application No. 131913, in particular in Example 1. In No. 131913, Example 1, the mixture containing paraffinsulfonic acids, unreacted n-paraffins, $H_2O$ and $H_2SO_4$ is treated with isopropanol in a quantity of 15%, to separate the mixture into three distinct phases; the upper one essentially consisting of n-paraffins, the lower one consisting of $H_2O$, $H_2SO_4$ and isopropanol, and the intermediate one containing paraffinsulfonic acids, $H_2SO_4$, $H_2O$, n-paraffins and isopropanol.

The intermediate phase is then mixed with methylene chloride to separate an aqueous $H_2SO_4$ phase containing isopropanol and a little methylene chloride from a phase containing paraffinsulfonic acids, n-paraffins, $H_2O$, methylene chloride and $H_2SO_4$. It is neutralized with soda and concentrated. Finally it is heated to a temperature of 200° C. to distill off the n-paraffins.

This procedure for removing the n-paraffins is obviously complicated, and notwithstanding its various extraction stages it is still necessary to use high-temperature vaporization at the end, which in all cases damages the product obtained.

With the known process it is therefore not possible to prepare free paraffinsulfonic acids or their salts with weak bases, as these are unstable at high temperature.

It has been surprisingly found that the previously described drawbacks of the known art regarding the separation of n-paraffins can be obviated in a simple manner by adding $H_2SO_4$ to the mixture of paraffinsulfonic acids, $H_2SO_4$, $H_2O$ and paraffins until a two-phase system forms or at least until the mixture becomes turbid. Then the turbid mixture or the supernatant phase of the two-phase system is extracted with carbon dioxide ($CO_2$) under supercritical conditions.

The present invention provides a process for removing n-paraffins containing between 12 and 18 carbon atoms from mixtures of said n-paraffins with paraffinsulfonic acids having the same number of carbon atoms, $H_2O$ and $H_2SO_4$. The mixtures are obtained by sulfoxidation of $C_{12}$–$C_{18}$ n-paraffin mixtures at a temperature of between 25° and 50° C. with $SO_2$ and $O_2$ in the presence of $H_2O$ and UV radiation. Excess $SO_2$, is removed if present, from the reaction mixture originating from the paraffinsulfonic acid synthesis reaction. The mixture is decanted to remove most of the $C_{12}$–$C_{18}$ n-paraffins. The characteristic of the process is that the residual mixture obtained after removing the $SO_2$ and the decanted paraffins is fed with $H_2SO_4$ until a two-phase system forms, or at least until the residual mixture becomes turbid. The turbid mixture or the supernatant phase of the two-phase system is then extracted with supercritical $CO_2$.

With regard to the quality of $H_2SO_4$ used according to the invention to form the two-phase system, this can be oleum, concentrated $H_2SO_4$ or $H_2SO_4$ diluted with $H_2O$ to a minimum $H_2SO_4$ concentration of 20% by weight. With regard to the formation of the two-phase system due to the addition of $H_2SO_4$, it commences with the mixture becoming turbid and proceeds as further $H_2SO_4$ is added, to give sharp separation of a heavy phase consisting of $H_2O$ and $H_2SO_4$ from a supernatant phase.

The mixture to be subjected to extraction with supercritical $CO_2$ is either the turbid mixture formed by adding the minimum quantity of $H_2SO_4$ or the supernatant mixture after separation from the heavy mixture of $H_2SO_4$ and $H_2O$ obtained by adding $H_2SO_4$ in a quantity exceeding the minimum, this latter as stated being that required to cause mixture turbidity. With 96% $H_2SO_4$, the weight ratio of $H_2SO_4$ to residual mixture can attain a value of 1:1 or higher.

With regard to the conditions under which the turbid or aforesaid supernatant mixture is extracted with supercritical $CO_2$, these are as follows:

| | |
|---|---|
| Extraction temperature: | between 32 and 80° C. |
| Extraction pressure: | between 75 and 350 bar |
| Weight ratio of $CO_2$ used for extraction to | |

The paraffinsulfonic acid mixture resulting from the process according to the present invention is then generally neutralized in known manner using chosen bases to thus obtain paraffin sulfonates of any desired type.

The $H_2SO_4$ contained in the mixture resulting from the process of the present invention, in the case of extraction of the supernatant phase with supercritical $CO_2$, is less in quantity than that present before the treatment and can be separated, if required, by methods known in the art, such as mixing with suitable substances or precipitation to form insoluble salts. Some examples are given hereinafter to better illustrate the invention, but without intending to limit it thereto or thereby.

EXAMPLE 1

A laboratory extraction apparatus was used consisting essentially of an extraction vessel into which the mixture containing the product to be extracted with supercritical $CO_2$ was fed, and a separator from which the $CO_2$, separated from the extracted substance, was recycled to the extractor by a metering pump after condensation.

401.0 g of crude mixture (with decantable n-paraffins and $SO_2$ removed) of paraffinsulfonic acids obtained by sulfoxidation of $C_{12}$–$C_{18}$ n-paraffins, and having the following composition:

| paraffinsulfonic acids | 24.74% by weight |
| --- | --- |
| $C_{12}-C_{18}$ n-paraffins | 26.46% by weight |
| $H_2O$ | 40.94% by weight |
| $H_2SO_4$ | 7.86% by weight | were treated with 80.0 g of 96 wt % $H_2SO_4$ at ambient temperature in a separator funnel.

After decantation, two phases were separated. The lower phase (213.5 g) consisted of $H_2O$ and $H_2SO_4$; the upper phase (267.5 g) contained all the n-paraffins and paraffinsulfonic acids present in the feed, together with $H_2O$ and $H_2SO_4$.

105.8 g of the upper phase product were extracted with supercritical $CO_2$.

The extraction was effected at 45° C. at 150 bar; the $CO_2$ throughput was maintained constant at 1.72 kg/h. After one hour, the $CO_2$ feed was interrupted and the refined product contained in the extractor was discharged.

Analysis of this product gave the following results:

| paraffinsulfonic acids | 62.29% by weight |
| --- | --- |
| $C_{12}-C_{18}$ n-paraffins | 0.11% by weight |
| $H_2O$ | 26.47% by weight |
| $H_2SO_4$ | 11.13% by weight |

The extracted n-paraffins are practically pure and can be recycled to the sulfoxidation reaction without any treatment.

EXAMPLE 2

3149.7 g of a crude mixture (as heretofore defined) of paraffinsulfonic acids having the composition indicated in Example 1 were treated with 158.1 g of 96 wt % $H_2SO_4$. After separating the lower phase (92.6 g) consisting of $H_2O$ and $H_2SO_4$, the upper phase was again treated with 96 wt % $H_2SO_4$ (161.1 g). A lower phase was separated (827.2 g) consisting of $H_2O$ and $H_2SO_4$, and the upper phase was again treated with 160.3 g of 96 wt % $H_2SO_4$. A lower phase was separated (392.4 g) consisting of $H_2O$ and $H_2SO_4$ sulphuric acid. The resultant upper phase (1918.1 g) was extracted with supercritical $CO_2$. Fifteen extraction tests were carried out, feeding about 120 g of product into the extractor for each test.

Extraction was effected at 45° C., 150 bar, with a $CO_2$ throughput of 1.72 kg/h and an extraction time of 2 hours. After each test the refined product and the extracted paraffins are discharged, and the extractor was fed with a new charge of material to be extracted.

The refined products and extracts of all the 15 tests were pooled and analysed.

Analysis of the refined product gave the following values:

| paraffinsulfonic acids | 69.73% by weight |
| --- | --- |
| $C_{12}-C_{18}$ n-paraffins | 0.55% by weight |
| $H_2O$ | 19.58% by weight |
| $H_2SO_4$ | 10.14% by weight |

EXAMPLE 3

200.2 g of a crude mixture (as heretofore defined) of paraffinsulfonic acids having the composition indicated in Example 1 were treated at ambient temperature with 32.2 g of 96 wt % $H_2SO_4$.

After separating the lower phase (88.8 g), a fraction of the upper phase (102.5 g) was extracted with supercritical $CO_2$ under the conditions described in Example 2.

Analysis of the refined product gave the following values:

| paraffinsulfonic acids | 60.55% by weight |
| --- | --- |
| $C_{12}-C_{18}$ paraffins | 0.09% by weight |
| $H_2O$ | 27.77% by weight |
| $H_2SO_4$ | 11.59% by weight |

EXAMPLE 4

199.9 g of a crude mixture (as heretofore defined) of paraffinsulfonic acids having the composition indicated in Example 1 were treated at ambient temperature with 16.75 g of 96 wt % $H_2SO_4$.

A lower phase was separated (45.4 g) consisting of $H_2O$ and $H_2SO_4$, and the upper phase containing all the paraffinsulfonic acids and paraffins present in the initial crude mixture was extracted with supercritical $CO_2$ under the conditions described in Example 2.

Analysis of the refined product gave the following values:

| paraffinsulfonic acids | 43.98% by weight |
| --- | --- |
| $C_{12}-C_{18}$ paraffins | 0.07% by weight |
| $H_2O$ | 39.89% by weight |
| $H_2SO_4$ | 16.06% by weight |

EXAMPLE 5

96 wt % $H_2SO_4$ was added to 200.3 g of a crude mixture (as heretofore defined) of paraffinsulfonic acids having the composition indicated in Example 1 and kept under efficient agitation at 22° C., until persistent turbidity was obtained at 22° C.

The quantity of $H_2SO_4$ added was 9.65 g. 114.6 g of this mixture were extracted with supercritical $CO_2$ under the conditions described in Example 2.

Analysis of the refined product gave the following values:

| paraffinsulfonic acids | 33.72% by weight |
| --- | --- |
| $C_{12}-C_{18}$ n-paraffins | 0.28% by weight |
| $H_2O$ | 50.12% by weight |
| $H_2SO_4$ | 15.88% by weight |

EXAMPLE 6

96 wt % $H_2SO_4$ was added to 200.5 g of a crude mixture (as heretofore defined) of paraffinsulfonic acids having the composition indicated in Example 1 and kept under efficient agitation at 45° C., until persistent turbidity was obtained at 45° C.

The quantity of $H_2SO_4$ added was 6.10 g. 119.25 g of this mixture were extracted with supercritical $CO_2$ under the conditions described in Example 2.

Analysis of the refined product gave the following values:

| paraffinsulfonic acids | 33.53% by weight |
| --- | --- |
| $C_{12}-C_{18}$ n-paraffins | 1.49% by weight |

|  |  |
|---|---|
| $H_2O$ | 49.38% by weight |
| $H_2SO_4$ | 15.60% by weight |

EXAMPLE 7

200.1 g of a crude mixture (as heretofore defined) of paraffinsulfonic acids having the composition indicated in Example 1 were treated at ambient temperature with 54.6 g of 70% $H_2SO_4$ (aqueous solution). A lower phase was separated (107.5 g) consisting of $H_2O$ and $H_2SO_4$.

127.2 g of the upper phase were extracted with supercritical $CO_2$ under the conditions described in Example 2.

Analysis of the refined product gave the following values:

|  |  |
|---|---|
| paraffinsulfonic acids | 58.185% by weight |
| $C_{12}$–$C_{18}$ n-paraffins | 0.025% by weight |
| $H_2O$ | 29.680% by weight |
| $H_2SO_4$ | 12.110% by weight |

EXAMPLE 8 (Comparative example without $H_2SO_4$ addition)

76.1 g of a crude mixture (as heretofore defined) of paraffinsulfonic acids having the composition indicated in Example 1 were extracted with supercritical $CO_2$ under the conditions described in Example 2.

Analysis of the refined product gave the following values:

|  |  |
|---|---|
| paraffinsulfonic acids | 33.33% by weight |
| $C_{12}$–$C_{18}$ paraffins | 8.99% by weight |
| $H_2O$ | 47.11% by weight |
| $H_2SO_4$ | 10.60% by weight |

In this case the paraffin extraction was found to be totally insufficient.

EXAMPLES 9–16 (Comparative examples without $H_2SO_4$ addition)

The crude mixture (as heretofore defined) of paraffinsulfonic acids having the composition indicated in Example 1 was extracted with supercritical $CO_2$ under various operating conditions. The operating conditions used and the results of the analyses carried out on the refined products are given in Table 1.

fins at a temperature of between 25°–50° C. with sulfur dioxide and oxygen in the presence of water and ultraviolet radiation, comprising the steps of;
 (a) removing excess sulfur dioxide, if present, from said reaction mixture,
 (b) decanting said reaction mixture to remove most of the $C_{12}$–$C_{18}$ paraffins and to obtain a residual mixture,
 (c) adding sulfuric acid to said residual mixture until a two-phase system forms, or at least until said residual mixture becomes a turbid mixture,
 (d) separating a supernatant phase from said two-phase system, and
 (e) extracting said turbid mixture or said supernatant phase with supercritical carbon dioxide.

2. A process as claimed in claim 1, wherein the quantity of sulfuric acid added is that minimum quantity which causes said residual mixture to become turbid.

3. A process as claimed in claim 1, wherein the sulfuric acid is oleum, concentrated sulfuric acid, or sulfuric acid diluted with water to a minimum concentration of 20% by weight.

4. A process as claimed in claim 1 and 3, wherein with 96% sulfuric acid the weight ratio of sulfuric acid to said residual mixture is at least 1:1.

5. A process as claimed in claim 1, wherein said extraction with supercritical carbon dioxide is carried out at a pressure of between 75 and 350 bar, a temperature of between 32° C.–80° C. and a weight ratio of carbon dioxide to paraffinsulfonic acids of between 1:1 and 50:1.

6. A process as claimed in claim 1, wherein about 96 wt % of sulfuric acid is added to said residual mixture until a two-phase system forms.

7. A process as claimed in claim 6, wherein said supernatant phase of said two-phase system, is extracted with supercritical carbon dioxide and the refined product contains between about 0.1–0.6 wt % $C_{12}$–$C_{18}$ n-paraffins.

8. A process as claimed in claim 1, wherein about 96 wt % of sulfuric acid is added to said residual mixture until said residual mixture becomes a turbid mixture.

9. A process as claimed in claim 8, wherein said turbid mixture is extracted with supercritical carbon dioxide and the refined product contains between about 0.3–1.5 wt % $C_{12}$–$C_{18}$ n-paraffins.

10. A process as claimed in claim 1, wherein about 70 wt % of sulfuric acid is added to said residual mixture until a two-phase system forms.

11. A process as claimed in claim 10, wherein said

TABLE 1

| EXAMPLE No. | MIXTURE FED g | EXTRACTION TEMP. °C. | EXTRACTION PRESSURE bar | EXTRACTION TIME hours | $CO_2$ RATE kg/h | ANALYSIS OF REFINED PRODUCT % WT | | | |
|---|---|---|---|---|---|---|---|---|---|
|  |  |  |  |  |  | PARAFFIN-SULFONIC ACIDS | PARAFFINS | WATER | SULFURIC ACID |
| 9 | 124.1 | 33 | 300 | 1 | 1.07 | 28.74 | 18.56 | 43.79 | 8.91 |
| 10 | 125.2 | 35 | 150 | 1 | 1.80 | 27.80 | 14.84 | 46.84 | 10.52 |
| 11 | 125.9 | 40 | 150 | 1 | 1.80 | 28.65 | 11.55 | 49.70 | 10.10 |
| 12 | 124.2 | 40 | 150 | 3 | 1.80 | 31.99 | 11.37 | 45.94 | 10.70 |
| 13 | 124.3 | 40 | 300 | 2 | 1.40 | 29.50 | 11.22 | 48.67 | 10.61 |
| 14 | 123.9 | 45 | 200 | 1 | 1.46 | 31.40 | 11.95 | 46.78 | 9.87 |
| 15 | 124.3 | 50 | 350 | 1 | 1.11 | 32.82 | 8.20 | 48.50 | 10.48 |
| 16 | 124.2 | 86 | 300 | 2 | 1.07 | 43.80 | 2.21 | 45.18 | 8.81 |

We claim:

1. A process for extracting $C_{12}$–$C_{18}$ n-paraffins from a reaction mixture of $C_{12}$–$C_{18}$ n-paraffins with paraffinsulfonic acids having the same number of carbon atoms, water and sulfuric acid, where said reaction mixture is obtained by sulfoxidation of a mixture of $C_{12}$–$C_{18}$ parafsupernatant phase of said two-phase system, is extracted with supercritical carbon dioxide and the refined product contains about 0.02 wt % $C_{12}$–$C_{18}$ n-paraffins.

* * * * *